United States Patent [19]

Cobb

[11] 4,146,552

[45] Mar. 27, 1979

[54] DEHYDROGENATION OF CIS-1,2-DICYANOCYCLOALKANE

[75] Inventor: Raymond L. Cobb, Bartlesville, Okla.

[73] Assignee: Phillips Petroleum Company, Bartlesville, Okla.

[21] Appl. No.: 841,514

[22] Filed: Oct. 12, 1977

[51] Int. Cl.$^2$ .................. C07C 120/00; C07C 121/48
[52] U.S. Cl. ............................... 260/464; 260/465 H
[58] Field of Search ........................... 260/464, 465 H

[56] References Cited

U.S. PATENT DOCUMENTS

| | | | |
|---|---|---|---|
| 3,268,611 | 8/1966 | Bajars | 260/680 |
| 3,275,706 | 9/1966 | Stapp | 260/683.15 |
| 3,336,354 | 8/1967 | Greene et al. | 260/464 |
| 3,998,853 | 12/1976 | Cobb | 260/346.2 M |
| 3,998,998 | 12/1976 | Uraneck et al. | 526/295 |
| 4,005,031 | 1/1977 | Surmatis | 260/603 C X |

OTHER PUBLICATIONS

C.A. 68, (1968), 86544u (Sugita).
Konaka et al., J. Org. Chem., vol. 34, (1969) pp. 1334–1337.
Nakagawa et al., J. Org. Chem., vol. 27, (1962) pp. 1597–1601.

*Primary Examiner*—Joseph Paul Brust

[57] ABSTRACT cis-1,2-Dicyanocycloalkanes are dehydrogenated by reaction with nickel peroxide.

4 Claims, No Drawings

DEHYDROGENATION OF CIS-1,2-DICYANOCYCLOALKANE

This invention relates to the dehydrogenation of a cis-1,2-dicyanocycloalkane. More particularly, it relates to such a dehydrogenation using nickel peroxide.

In one of its concepts, the invention provides a reaction for the dehydrogenation of a cis-1,2-dicyanocycloalkane to yield a 1,2-dicyanocycloalkene. In another of its concepts, the invention provides such a process for reaction using a nickel peroxide reactant.

1,2-Dicyanocycloalkanes are useful, as such, and as intermediates for the preparation of other useful products. By way of example, 1,2-dicyanocyclobutene is useful as a nematocide and as an intermediate for the preparation of clathrates. After thermal isomerization to 2,3-dicyano-1,3-butadiene, the latter is useful for copolymerization to yield polymers with useful properties. 1,2-Dicyanocyclohexene can be hydrolyzed to cyclohexene-1,2-dicarboxylic acid. The acid reacts with polyhydric alcohols to yield polyesters with useful properties.

1,2-Dicyanocyclobutane is commercially available as a mixture of cis- and trans-isomers. These isomers are separated by fractional distillation. Nickel peroxide was prepared by the method of Nakagawa et al using nickel sulfate hydrate, sodium hypochlorite solution and sodium hydroxide.

It is an object of this invention to dehydrogenate cis-1,2-dicyanocycloalkanes. It is another object of this invention to prepare 1,2-dicyanocycloalkenes. It is a further object of this invention to provide a process for the intramolecular dehydrogeneration of cis-1,2-dicyanocycloalkane. It is a further object of this invention to perform such a dehydrogenation to yield 1,2-dicyanocycloalkene.

Other aspects, concepts, and the several advantages of the invention are apparent from a study of this disclosure and the appended claims.

According to the present invention, a process for the intramolecular dehydrogenation of cis-1,2-dicyanocycloalkane is provided to yield 1,2-dicyanocycloalkene by reaction with nickel peroxide as described herein.

cis-1,2-Dicyanocycloalkanes containing up to 30 carbon atoms which can be represented by the following general formula:

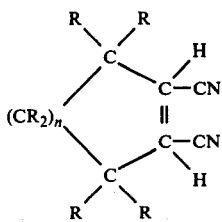

wherein each R is selected from a group consisting of hydrogen, alkyl radicals of 1 to 10 carbon atoms, aryl or substituted aryl radicals of 6 to 12 carbon atoms, or aralkyl radicals of 7 to 12 carbon atoms, n is 0 or an integer from 1 to 6, and the two cyano groups are in the cis configuration, can be dehydrogenated to produce a 1,2-dicyanocycloalkene which can be represented by the general formula:

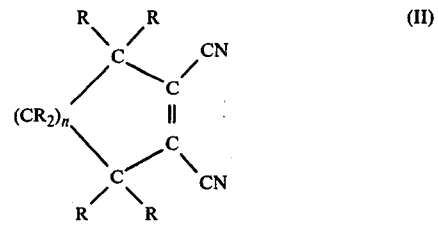

wherein R and n are as defined above.

Specific examples of the reactants of this invention include cis-1,2-dicyanocyclobutane, cis-1,2-dicyano-3-methylcyclobutane, cis-1,2-dicyanocyclopentane, cis-1,2-dicyanocyclohexane, cis-1,2-dicyanocyclooctane, cis-1,2-dicyanocyclodecane, cis-1,2-dicyano-3,4-dimethylcyclobutane, 3-benzyl-cis-1,2-dicyanocyclobutane, cis-1,2-dicyano-3-phenylcyclobutane, and the like.

A currently preferred class of reactants for the practice of this invention is the cis-1,2-dicyanocyclobutanes (I, n=0) represented by the following general formula

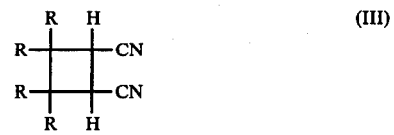

wherein each R is selected from the group described above. The now preferred compound for the dehydrogenation reaction of this invention is cis-1,2-dicyanocyclobutane (III, R=H).

cis-1,2-Dicyanocyclobutane is commercially available and is prepared by the dimerization of acrylonitrile.

The attempted reaction of trans-1,2-dicyanocyclobutane with nickel peroxide under the conditions of this invention was found to yield only small amounts of 1,2-dicyanocyclobutene.

It is not known at this time whether the product is formed directly from the trans-isomer, from cis-isomer impurity in the trans-isomer or from a slow trans- to cis-isomerization followed by reaction of the cis-isomer.

According to the invention, the cis-1,2-dicyanocycloalkane (I) is reacted with nickel peroxide. Said nickel peroxide can be prepared by the method of Nakagawa et al [K. Nakagawa, R. Konaka, and T. Nakata, J. Org. Chem., 27, 1597 (1962)], or by other methods that give nickel peroxide as the active component. The nickel peroxide can be used by itself or supported on a solid support (U.S. Pat. No. 4,005,031, Surmatis, issued Jan. 25, 1977). Nickel peroxide prepared by Nakagawa's method is a black, hydrous oxide with a composition of $NiO_{2.77}H_{2.85}$ [R. Konaka, S. Terabe, and K. Kuruma, J. Org. Chem., 34, 1334 (1969)]. The nickel peroxide is preferably prepared and separated from the peroxide preparation mixture and then used for the reaction of this invention.

The amount of nickel peroxide to be used in the practice of this invention will be broadly 0.05 to 1.4, preferably 0.1 to 1.0 g of nickel peroxide per mmole of cis-1,2-dicyanocycloalkane. Higher levels of nickel peroxide have been found to be detrimental to the reaction of this invention.

The process of this invention can be carried out in the temperature range of broadly 50° C. to 150° C. and preferably 75° C. to 120° C.

The reaction pressure is not critical although atmospheric or superatmospheric pressures are usually used.

Although not required, an inert atmosphere above the reaction mixture is preferred and may be provided by using inert gases such as nitrogen, argon, and the like.

The time utilized for the reaction depends on the temperature, catalyst level, reactant, etc., and, therefore, can vary from a few minutes to several hours or longer.

The reaction mixture of this invention is normally heterogeneous and conventional mixing techniques are normally used during the reaction period.

The diluent used in the reaction of this invention can be selected from a group consisting of alkanes, cycloalkanes, aromatics, and substituted aromatics that are liquids at the temperature used for the reaction. Specific examples of suitable diluents include hexane, 3-methylhexane, n-octane, n-decane, cyclohexane, benzene, toluene, chlorobenzene, anisole, and the like. The amount of diluent will be broadly 0.1 to 30 and preferably 0.5 to 15 g of diluent per mmole of starting dicyano compound. Other diluents not adversely affecting the reaction of the invention can be employed.

The order of addition of dicyano compound, diluent, and nickel peroxide is not considered critical.

The reaction mixture obtained by the reaction of this invention is normally filtered, distilled at atmospheric or reduced pressure to remove the diluent, and the residue distilled or crystallized to isolate the reaction product. However, other suitable techniques can be employed for the separation and purification of the reaction product.

EXAMPLE I

A round bottom flask equipped with a reflux condenser and stirrer was charged with 5 g (47 mmole) cis-1,2-dicyanocyclobutane, 150 ml (132 g) benzene, and 10 g nickel peroxide. The mixture was refluxed with stirring for 24 hours. Analysis of the mixture by glc showed that it contained 11.6 weight percent 1,2-dicyanocyclobutene, 1.87 weight percent trans-1,2-dicyanocyclobutane, and 86.53 weight percent cis-1,2-dicyanocyclobutane.

EXAMPLE II

When the above reaction was attempted with 5 g (47 mmole) trans-1,2-dicyanocyclobutane, the mixture after refluxing for 24 hours contained only two weight percent 1,2-dicyanocyclobutene and 98 weight percent starting material.

Therefore, the reaction of this invention appears to occur preferentially with the cis-isomer. It occurs only to a slight extent with the trans-isomer.

EXAMPLE III

A round bottom flask equipped with a reflux condenser and stirrer was charged with 1.0 g (9.4 mmole) cis-1,2-dicyanocyclobutane, 150 ml (132 g) benzene, and 15 g nickel peroxide. The mixture was refluxed with stirring for 30 minutes. Analysis of the mixture by glc showed that the starting material was no longer present and no volatile products were formed.

The results of this run show that high ratios of nickel peroxide to cis-1,2-dicyanocyclobutane are detrimental to the reaction of this invention.

EXAMPLE IV

A round bottom flask equipped with a reflux condenser and stirrer was charged with 2.0 g (19 mmole) cis-1,2-dicyanocyclobutane, and 30 to 40 ml benzene. Nickel peroxide was added in ca. 1.5 g portions over a 4–5 hour period to the refluxing reaction mixture until a total of 10.31 g had been added. The mixture was filtered and the benzene distilled under reduced pressure to yield an orange oil. An NMR analysis showed the oil to contain about 30 weight percent 1,2-dicyanocyclobutene and about 70 weight percent cis- and trans-1,2-dicyanocyclobutanes.

EXAMPLE V

A round bottom flask equipped with a reflux condenser and stirrer was charged with 10 g (9.4 mmole) cis-1,2-dicyanocyclobutane, 150 ml (132 g) benzene, and 25 g (95 mmole) nickel sulfate (NiSO$_4$·6H$_2$O) in 150 ml water. The mixture was stirred vigorously at 50° C. and a solution of 4 g (100 mmole) sodium hydroxide in 200 ml of a six percent sodium hypochlorite solution was added dropwise. The mixture was stirred at 50° C. for six hours and allowed to stand overnight at 25° C. The mixture was filtered and the solid washed with benzene. The benzene layer was separated from the aqueous layer and distilled under reduced pressure to yield about 9.5 g of a yellow oil. An analysis of the oil by glc showed that the oil was cis-1,2-dicyanocyclobutane containing trace amounts of the trans-isomer and 1,2-dicyanocyclobutene.

The results of this run show that very little of the reaction of this invention occurs under these conditions when the nickel peroxide is prepared in the presence of the dicyano reactant. However, it is now believed that under optimum conditions this method of nickel peroxide preparation and reaction with cis-1,2-dicyanocyclobutane would yield larger amounts of 1,2-dicyanocyclobutene.

Reasonable variation and modification are possible within the scope of the foregoing disclosure and the appended claims to the invention, the essence of which is that a cis-1,2-dicyanocycloalkane, as described, has been dehydrogenated to yield a 1,2-dicyanocycloalkene, also as described, in the presence of nickel peroxide.

I claim:

1. The dehydrogenation of a cis-1,2-dicyanocycloalkane wherein the cis-1,2-dicyanocycloalkane contains up to 30 carbon atoms and is represented by the following formula:

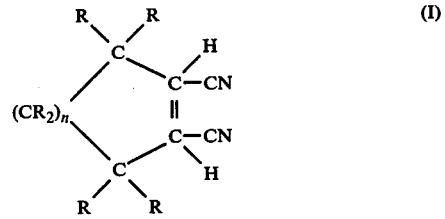

wherein each R is selected from a group consisting of hydrogen, alkyl radicals of 1 to 10 carbon atoms, aryl radicals of 6 to 12 carbon atoms, or aralkyl radicals of 7 to 12 carbon atoms, n is 0 or an integer from 1 to 6, and the two cyano groups are in the cis configuration, in the presence of nickel peroxide and wherein a product formed during the dehydrogenation is a 1,2-dicyanocycloalkene which is represented by the general formula:

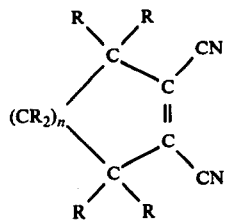

wherein R and n are as defined herein, which comprises employing the nickel peroxide in the approximate range of from about 0.05 to about 1.4 grams of nickel peroxide per mmole of cis-1,2-dicyanocycloalkane at a temperature in the approximate range of from about 50° C. to about 150° C.

2. A process according to claim 1 wherein the cis-1,2-dicyanocycloalkane is represented by the following general formula

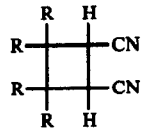

wherein each R is selected as described in claim 1.

3. A process according to claim 2 wherein the compound dehydrogenated is selected from the following; cis-1,2-dicyanocyclobutane, cis-1,2-dicyano-3-methylcyclobutane, cis-1,2-dicyanocyclopentane, cis-1,2-dicyanocyclohexane, cis-1,2-dicyanocyclooctane, cis-1,2-dicyanocyclodecane, cis-1,2-dicyano-3,4-dimethylcyclobutane, 3-benzyl-cis-1,2-dicyanocyclobutane and cis-1,2-dicyano-3-phenylcyclobutane.

4. A process according to claim 1 wherein the compound dehydrogenated is cis-1,2-dicyanocyclobutane.

* * * * *

UNITED STATES PATENT AND TRADEMARK OFFICE
CERTIFICATE OF CORRECTION

PATENT NO. : 4,146,552
DATED : March 27, 1979
INVENTOR(S) : Raymond L. Cobb

It is certified that error appears in the above-identified patent and that said Letters Patent are hereby corrected as shown below:

In Column 1, line 55, in Formula I the double bond ( || ) joining the two carbons should be a single bond ( | ).

In Column 4, line 57, in Formula I the double bond ( || ) joining the two carbons should be a single bond ( | ).

Signed and Sealed this

Fourteenth Day of August 1979

[SEAL]

Attest:

Attesting Officer

LUTRELLE F. PARKER
Acting Commissioner of Patents and Trademarks